US006703041B2

(12) United States Patent
Burns et al.

(10) Patent No.: US 6,703,041 B2
(45) Date of Patent: Mar. 9, 2004

(54) COMPOSITIONS CONTAINING POLYANIONIC POLYSACCHARIDES AND HYDROPHOBIC BIOABSORBABLE POLYMERS

(75) Inventors: James W. Burns, Boston, MA (US); Keith E. Greenawalt, Milton, MA (US); Louis Masi, Boston, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 09/946,121

(22) Filed: Sep. 4, 2001

(65) Prior Publication Data

US 2002/0018813 A1 Feb. 14, 2002

Related U.S. Application Data

(63) Continuation of application No. 08/318,987, filed on Oct. 6, 1994, now Pat. No. 6,294,202.

(51) Int. Cl.[7] .............................. A61K 9/70; A61K 9/10; A61K 47/36
(52) U.S. Cl. ....................... 424/444; 424/402; 424/488; 424/443
(58) Field of Search ........................... 424/488, 443–44, 424/426, 400, 402; 514/777, 54

(56) References Cited

U.S. PATENT DOCUMENTS

| 3,792,010 A | 2/1974 | Wasserman et al. |
| 3,839,297 A | 10/1974 | Wasserman et al. |
| 3,998,974 A | 12/1976 | Zaffaroni |
| 4,060,081 A | 11/1977 | Yannas et al. |
| 4,233,969 A | 11/1980 | Lock et al. |
| 4,280,954 A | 7/1981 | Yannas et al. |
| 4,343,736 A | 8/1982 | Uemura et al. |
| 4,458,678 A | 7/1984 | Yannas et al. |
| 4,487,865 A | 12/1984 | Balazs et al. |
| 4,526,714 A | 7/1985 | Feijen et al. |
| 4,582,865 A | 4/1986 | Balazs et al. ................. 524/29 |
| 4,774,093 A | 9/1988 | Provonchee et al. ........ 424/493 |
| 4,810,784 A | 3/1989 | Larm |
| 4,937,270 A | 6/1990 | Hamilton et al. |
| 4,970,298 A | 11/1990 | Silver et al. |
| 4,973,493 A | 11/1990 | Guire |
| 5,017,229 A | 5/1991 | Burns et al. |
| 5,147,401 A | 9/1992 | Bakker et al. |
| 5,366,508 A | 11/1994 | Brekke |
| 5,447,940 A | 9/1995 | Harvey et al. |
| 5,520,916 A | 5/1996 | Dorigatti et al. |
| 5,644,049 A | 7/1997 | Giusti et al. |
| 5,760,200 A | 6/1998 | Miller et al. |
| 5,766,631 A | 6/1998 | Arnold et al. |
| 6,030,958 A | 2/2000 | Burns et al. |

FOREIGN PATENT DOCUMENTS

| CA | 2022091 | 2/1991 |
| EP | 0193510 | 9/1986 |
| EP | 0 224 987 | 6/1987 |
| EP | 2 244 178 | 11/1987 |
| EP | 0 291 177 | 11/1988 |
| EP | 0416250 A2 | 3/1991 |
| EP | 0 705 838 A3 | 10/1995 |
| EP | 0 705 838 A2 | 10/1995 |
| GB | 2151244 A | 7/1985 |
| WO | 8600079 | 1/1986 |
| WO | 8600912 | 2/1986 |
| WO | WO 94/01468 | 1/1994 |
| WO | WO 94/21299 | 9/1994 |
| WO | WO 96/02286 A1 | 2/1996 |

OTHER PUBLICATIONS

Sparer et al., "Controlled Release from Glycosaminoglycan Drug Complexes", Controlled Release Delivery System, Marcel Dekker, Inc. (New York) pp. 107–119, 1983.
Danishefsky et al., "Conversion of Carboxyl Groups of Mucopolysaccharides into Amides of Amino Acid Esters", Carbohydrate Research—16:199–205, 1971.
Laurent et al., "Cross–Linked Gels of Hyaluronic acid", Acta Chemical Scandinavia; 18:71–282; 1964.
Pouyani et al., "Solid–State NMR of N–Acylureas Derived from the Reaction of Hyaluronic Acid with Isotopically–Labeled Carbodiimides,".
Kuo et al., "Chemical Modification of Hyaluronic Acid by Carbodiimides," Bioconjugate Chem. 2:232–241, 1991.
Staros, Accts. Chem. Res. 21:435, 1988, "Membrane–Impermeant Cross–Linking Reagents: Probes of the Structure and Dynamics of Membrane Proteins."
Silverstein et al., eds., *Spectrometric Identification of Organic Compounds*, pp. 122–124, J. Wiley & Sons, New York, 1981.
Sheehan et al., "Hyaluronic Acid: a Double–helical Structure in the Presence of Potassium at Low pH and Found also with the Cations Ammonium, Rubidium and Caesium," J. Mol. Biol. 117:113–135, 1977.
Goodman & Gillman's *The Pharmacological Basis of Therapeutics*, Gilman et al., eds., Pergamon Press, NY, 1990, p. 1313.
De Los et al., "Reactions of Carbodiimides. I. The Mechanisms of the Reactions of Acetic Acid with Dicyclohexylcarbodiimide," J. Am. Chem. Soc. 88:1013, 1967.
Rupprecht, A., Wet Spinning of Hyaluronic Acid. Preparation of Oriented Samples, Acta Chem. Scand., vol. 33, p. 779–780 (1979).
Dagalakis et al., Design of an artificial skin. Part III. Control of pore structure, J. of Biomed. Res., vol. 14, pp. 511–528 (1980).
Herman et al., Heparin–modified polylactide as biodegradable hemocompatible biomaterial, J. of Mater. Sci., Materials in Medicine, vol. 5, No. 9, pp. 728–731 (1994).
Goldberg et al., Prevention of Postoperative Adhesions By Precoating Tissues With Dilute Sodium Hyaluronate Solutions, Gynecologic Surgery and Adhesion Prevention, pp. 191–204(1993).

Primary Examiner—Edward J. Webman

(57) ABSTRACT

Biocompatible compositions comprising polyanionic polysaccharides combined with hydrophobic bioabsorbable polymers as well as methods for making and using the compositions are described.

61 Claims, No Drawings

COMPOSITIONS CONTAINING POLYANIONIC POLYSACCHARIDES AND HYDROPHOBIC BIOABSORBABLE POLYMERS

This application is a continuing application of Ser. No. 08/318,987 filed on Oct. 6, 1994 now issued as U.S. Pat. No. 6,294,202 B1.

BACKGROUND OF THE INVENTION

The present invention relates to water-insoluble biocompatible compositions formed from one or more chemically modified polyanionic polysaccharides, and more specifically to compositions of these chemically modified polyanionic polysaccharides and hydrophobic bioabsorbable polymers.

Polyanionic polysaccharides are polysaccharides, also called glycans, containing more than one negatively charged group (e.g., carboxyl groups at pH values above 4.0); they consist of long chains having hundreds or thousands of basic repeat units. These molecules may differ in the nature of their recurring repeat units, in the length of their chains, and in the degree of branching. There are two major types of polyanionic polysaccharides: homopolysaccharides, which contain only a single type of monomeric unit, and heteropolysaccharides, which contain two or more different types of monomeric units.

Polysaccharides naturally occur in a variety of tissues in the body and in some cases associate with proteins in complex macromolecular structures. Examples include proteoglycans, found in the jellylike ground substance, or extracellular matrix, filling the space between the cells of most tissues. Proteoglycans are also present in cartilage, tendons, skin, and in the synovial fluid. Likewise, glycosaminoglycans are water-soluble polysaccharides found in the ground substance of connective tissue, and are highly charged linear polyanions having the general formula $(AB)_n$, where A is a uronic acid residue and B is a hexosamine.

Hyaluronic acid (HA) and its salt sodium hyaluronate is an example of a naturally occurring glucosaminoglycan, or mucopolysaccharide that is a common extracellular matrix component. HA is ubiquitous within the human body and exists in a wide range of forms in a variety of tissues including synovial fluid, vitreous humor, blood vessel walls, pericardial fluid, and umbilical cord.

Hyaluronic acid in chemically modified ("derivatized") forms, is useful as a surgical aid, to prevent adhesions or accretions of body tissues during the post-operation period (e.g., U.S. Pat. No. 5,017,229). The derivatized HA in the form of a gel or membrane is placed over and between damaged tissue surfaces in order to prevent adhesion formation between apposing surfaces. To be effective, the gel or film must remain in place and prevent tissue contact for a long enough time so that when the gel finally disperses and the tissues do come into contact, they will no longer have a tendency to adhere.

Chemically modified HA can also be useful for controlled release drug delivery. Balazs et al., 1986, U.S. Pat. No. 4,582,865, states that "cross-linked gels of HA can slow down the release of a low molecular weight substance dispersed therein but not covalently attached to the gel macromolecular matrix." Sparer et al., 1983, Chapter 6, pages 107–119, in Roseman et al., *Controlled Release Delivery Systems*, Marcel Dekker, Inc., New York, describes sustained release of chloramphenicol covalently attached to hyaluronic acid via ester linkage, either directly or in an ester complex including an alanine bridge s an intermediate linking group.

Danishefsky et al., 1971, *Carbohydrate Res.*, Vol. 16, pages 199–205, describes modifying a mucopolysaccharide by converting the carboxyl groups of the mucopolysaccharide into substituted amides by reacting the mucopolysaccharide with an amino acid ester in the presence of 1-ethyl-3-(3-dimethylaminopropyl) carbodiimide hydrochloride ("EDC") in aqueous solution. They reacted glycine methyl ester with a variety of polysaccharides, including HA. The resulting products are water-soluble; that is, they rapidly disperse in water or in an aqueous environment such as is encountered between body tissues.

Proposals for rendering HA compositions less water-soluble include cross-linking the HA. R.V. Sparer et al., 1983, Chapter 6, pages 107–119, in T.J. Roseman et al., *Controlled Release Delivery Systems*, Marcel Dekker, Inc., New York, describe modifying HA by attaching cysteine residues to the HA via amide bonds and then cross-linking the cysteine-modified HA by forming disulfide bonds between the attached cysteine residues. The cysteine-modified HA was itself water-soluble and became water-insoluble only upon cross-linking by oxidation to the disulfide form.

De Belder et al., PCT Publication No. WO 86/00912, describe a slowly-degradable gel, for preventing tissue adhesions following surgery, prepared by cross-linking a carboxyl-containing polysaccharide with a bi- or polyfunctional epoxide. Other reactive bi- or polyfunctional reagents that have been proposed for preparing cross-linked gels of HA having reduced water-solubility include: 1,2,3,4-diepoxybutane in alkaline 3 medium at 50° C. (Laurent et al., 1964, *Acta Chem. Scand.*, vol. 18, page 274); divinyl sulfone in alkaline medium (Balazs et al., U.S. Pat. No. 4,582,865, (1986); and a variety of other reagents including formaldehyde, dimethylolurea, dimethylolethylene urea, ethylene oxide, a polyaziridine, and a polyisocyanate (Balasz et al., U.K. Patent Appl. No. 84 20 560 (1984). Malson et al., 1986, PCT Publication No. WO 86/00079, describe preparing cross-linked gels of HA for use as a vitreous humor substitute by reacting HA with a bi- or polyfunctional cross-linking reagent such as a di- or polyfunctional epoxide. Malson et al., 1986, EPO 0 193 510, describe preparing a shaped article by vacuum-drying or compressing a cross-linked HA gel.

SUMMARY OF THE INVENTION

In one aspect, the invention features a biocompatible composition containing one or more polyanionic polysaccharides combined with one or more hydrophobic bioabsorbable polymers or copolymers.

In preferred embodiments, the polyanionic polysaccharide is carboxymethylcellulose (CMC), carboxymethylamylose (CMA), hyaluronic acid (HA), chondroitin-6-sulfate, dermatin sulphate, heparin, heparin sulfate, heparan sulfate, or dermatin-6-sulfate. Preferably, the polyanionic polysaccharide is HA, CMC, or CMA. Most preferably, the polyanionic polysaccharide is in the form of a water-insoluble derivative. Also in preferred embodiments, the biocompatible composition includes two or more polyanionic polysaccharides or their water-insoluble derivatives, e.g., hyaluronic acid and carboxymethylcellulose or hyaluronic acid and heparin.

The hydrophobic bioabsorbable polymer is chosen from the group consisting of polyglycolide, polylactide (D, L, DL), polydioxanones, polyestercarbonates, polyhydroxyalkonates, polycaprolactone (polylactones), and copolymers thereof; preferably polyglycolide or polylactide, or a copolymer or polyglycolide-caprolactone of polyglycolide and polylactide, polylactide-polycaprolactone.

The compositions of the invention can be provided in the form of an adhesion prevention composition, e.g., in a membrane, foam, film, or composition suitable for extrusion. When the composition contains a water-insoluble polyanionic polysaccharide derivative the composition can also be produced in the form of fibers, or knitted or weaved fabric.

Compositions of the invention which contain a water-insoluble polyanionic polysaccharide derivative can also be provided as a composite matrix to support cell and tissue growth and proliferation. For example, any desired cell type may be cultured in vitro in the presence of one of the water-insoluble compositions of the present invention to form a water-insoluble matrix that is coated, impregnated or infiltrated with the cells. Preferably, the cells are derived from a mammal, and most preferably from a human. In one example, fibroblast infiltrated matrices may be placed at the site of a skin lesion (e.g., wound or ulcer) to promote healing of the lesion. Other cell types that can be cultured on the matrices of this invention include but are not limited to, osteocytes, chondrocytes, keratinocytes, and tenocytes. Matrices impregnated with these cells can be used to aid in the healing of bone, cartilage, skin, and tendons and ligaments, respectively. Matrices can also be generated which contain a mixture of cell types, e.g., to mimic the cellular makeup of a desired tissue. The matrices of this invention can also be seeded with non-differentiated mesenchymal cells that can differentiate into a variety of tissue specific types upon implantation, or seeded with fetal or neonatal cells of the desired type. One advantage associated with the use of the water-insoluble compositions as cellular matrices in vivo is that the matrix is completely biocompatible and is reabsorbed by the body. Alternatively, matrices impregnated with various cell types are useful for in vitro diagnostic applications. For example, matrices infiltrated with fibroblasts can be used to test the efficacy and/or toxicity of various pharmaceutical or cosmetic compounds.

The compositions of the invention may further include a drug for use as a drug delivery system. The particular drug used is a matter of choice depending on the intended use of the composition. Preferred drugs include, but are not limited to, proteins (e.g., growth factors, enzymes), steroids, non-steroidal anti-inflammatory drugs, cytotoxic agents (e.g., anti-tumor drugs), antibiotics, oligonucleotides (e.g., antisense), and biopolymers. When provided for cell and tissue growth and proliferation, the compositions of the invention may further include growth factors, and cell attachment proteins or peptides.

In a second aspect, the invention features a method of making a biocompatible composition by combining one or more polyanionic polysaccharides with a hydrophobic bioabsorbable polymer under conditions sufficient to form the biocompatible composition. Preferably, the polyanionic polysaccharide is in the form of a film or foam, and most preferably the polyanionic polysaccharide is in the form of a water-insoluble derivative.

In preferred embodiments of this aspect of the invention, methods for combining the hydrophobic bioabsorbable polymer and polyanionic polysaccharide include coating the polyanionic polysaccharide with the hydrophobic bioabsorbable polymer, e.g., by spraying or brushing the polyanionic polysaccharide with a hydrophobic bioabsorbable polymer solution; applying hydrophobic bioabsorbable polymer coating to only one side of the polyanionic polysaccharide composition; admixing the hydrophobic bioabsorbable polymer with a solution of the polyanionic polysaccharide composition; dispersing fibers of hydrophobic bioabsorbable polymer into a solution of the polyanionic polysaccharide composition; and compressing a film of the hydrophobic bioabsorbable polymer onto the polyanionic polysaccharide composition, e.g., by heat compression with elevated temperature to ensure the hydrophobic polymer flows onto the polyanionic polysaccharide composition. When a water-insoluble derivative of a polyanionic polysaccharide is used, the method of the invention can also involve dipping the insoluble composition into a hydrophobic bioabsorbable polymer solution to coat both sides of the insoluble polyanionic polysaccharide composition simultaneously. After application of the hydrophobic bioabsorbable polymer, the composition is dried to remove solvent, leaving a polyanionic polysaccharide hydrophobic bioabsorbable polymer matrix.

The hydrophobic bioabsorbable polymer solution is made by dissolving the polymer, polymers, or copolymers in a volatile solvent such as methylene chloride at a concentration of 0.1 to 50% (w/w); preferably 0.5 to 20% (w/w); more preferably 0.5 to 5% (w/w); and most preferably 1.0 to 3.0% (w/w).

In another aspect, the invention features a method for promoting cell growth and proliferation in vitro. In this aspect, the method includes the steps of obtaining a sample of cells, admixing the cells with a water-insoluble biocompatible matrix containing a water-insoluble derivative of a polyanionic polysaccharide combined with a hydrophobic bioabsorbable polymer, and then culturing the admixture under conditions sufficient to promote growth and infiltration of the cells into the matrix. Cells which may be grown according to the method of the invention include any cell type which can be cultured in vitro; preferably, the cells are mammalian; and most preferably, they are derived from a human.

In still another aspect, the invention includes a method for promoting cell growth and proliferation in vivo at the site of an injury, e.g., in a mammal, preferably a human. This method includes the steps of obtaining a sample of cells capable of promoting healing of the injury, admixing the cells with a water-insoluble biocompatible matrix containing a water-insoluble derivative of a polyanionic polysaccharide combined with a hydrophobic bioabsorbable polymer, and placing the admixture at the site of injury in the mammal to promote growth and proliferation of cells at the site in order to facilitate the healing of the injury.

Embodiments of this aspect of the invention include obtaining the cell sample directly from the desired tissue and admixing the sample with the water-insoluble biocompatible matrix; obtaining the cell sample from the desired tissue and culturing the Cells in vitro prior to admixture with the water-insoluble biocompatible matrix; and obtaining the cell sample from an established cell line and admixing the cells with the water-insoluble biocompatible matrix. Preferably, the admixture containing the cell sample and the water-insoluble biocompatible matrix is cultured in vitro under conditions sufficient to promote proliferation and infiltration of the cells into the matrix prior to placement at the site of injury.

The cells admixed with the biocompatible matrix for this aspect of the invention can be of any cell type which is capable of supporting cell growth and proliferation at the site of injury. For example, the source of the cells can be xenogeneic to the mammal, but preferably the cells are allogeneic, and most preferably the cells are immunologically compatible with the mammal. Further, the infiltrated matrix can contain cells of the same cell type as the cells found at the site of injury (e.g., from the same tissue), or the matrix can contain cells which are of a different cell type but which deposit extracellular matrix components within the biocompatible matrix to serve as a scaffold for cell growth in vivo.

In preferred embodiments of this aspect of the invention, the cells are fibroblasts and the infiltrated matrix is placed at the site of a skin lesion (e.g., a wound, burn, surgical incision, or a dermal ulcer), the cells are osteocytes, and the infiltrated matrix is placed at the site of a bone injury; the cells are chondrocytes and the infiltrated matrix is placed at the site of an injury to cartilaginous tissue; the cells are keritinocytes and the infiltrated matrix is placed at the site of a skin lesion; the cells are tenocytes and the infiltrated matrix is placed at the site of an injury to a tendon; or the cells are non-differentiation mesenchymal cells.

The biocompatible matrix used in the methods of the invention can further contain one or more drugs, e.g., a growth factor to further enhance growth of the cells and/or an antibiotic to reduce the risk of infection at the site of placement.

By the phrase "immunologically compatible," as used herein, is meant that the cells are obtained from a histocompatible donor in order to minimize the probability of rejection by the immune system of the mammal being treated. Preferably, the cells are from an individual who has the same or a compatible HLA phenotype. Most preferably, the cells are obtained directly from the mammal to be treated.

A "polyanionic polysaccharide" (PAS) as the term is used herein, is a polysaccharide, including non-modified as well as chemical derivatives thereof, that contains more than one negatively charged group (e.g., carboxyl groups at pH values above about 4.0) and includes salts thereof, such as sodium or potassium salts, alkaline earth metal salts such as calcium or magnesium salts.

A "polyanionic polysaccharide derivative," as the term is used herein, is one or more polyanionic polysaccharides (PAS) that are chemically modified from the native form. Such modifications can include the addition of functional groups (e.g., substituted amide groups, ester linkages, and amine groups); reactions that increase the water insolubility of the PAS by covalently cross-linking the PAS molecules; and reactions that increase the water insolubility of the PAS by non-covalent interactions as described herein.

By "non-modified polyanionic polysaccharide" is meant a polyanionic polysaccharide with its native chemical structure intact.

The term "film," as used herein, means a substance formed by compressing a foam to a thin membrane, by casting into a flat mold and air drying to a thin membrane, or by compressing a gel or fibers, or by allowing or causing a gel or fibers to dehydrate.

The term "foam," as used herein, means a substance with a porous structure formed, for example, by lyophilization of the polyanionic polysaccharide solutions suspensions, gels, or fibers of the invention.

The term "hydrophobic," as used herein, refers to compounds or compositions which lack an affinity for water.

The term "bioabsorbable," as used herein, refers to the ability of a tissue-compatible material to degrade in the body after implantation, into nontoxic products which are eliminated from the body or metabolized (Barrows, "Synthetic Bioabsorbable Polymers," p. 243 In *High Performance Biomaterials—A Comprehensive Guide to Medical and Pharmaceutical Applications*, Michael Szycher, ed., Technomic Publishing: Lancaster, Pa., 1991).

The term "polymer" as used herein refers to a molecule made by the repetitive bonding of at least two, and preferably more than two, repeating monomeric smaller units (e.g., monosaccharide, amino acid, nucleotides, alkenes, or organic acid units). Accordingly, the term copolymer refers to a polymer formed by combination of two or more copolymerized monomeric or polymeric species.

A "biocompatible" substance, as the term is used herein, is one that has no medically unacceptable toxic or injurious effects on biological function.

A "water-soluble" film or foam, as the term is used herein, is one which, formed by drying an aqueous solution of 1% weight/weight ("w/w") unmodified polyanionic polysaccharide in water, and having dimensions 3 cm×3 cm×0.3 mm, when placed in a beaker of 50 ml distilled water at 20° C., and allowed to stand without stirring, loses its structural integrity as a film after 3 minutes, and becomes totally dispersed within 20 minutes. A "water-insoluble" film as used herein of the invention, as that phrase and like terms are used herein, is formed using a 1% aqueous solution of a polyanionic polysaccharide, modified as previously described, having the same dimensions and similarly allowed to stand without stirring in a beaker of 50 ml distilled water at 20° C., is structurally intact after 20 minutes; the film boundaries and edges are still present after 24 hours.

The foams, films, and other forms of the invention can be prepared in colored form, by including a dye or stain in the reaction mixture. Such colored films and gels can be more easily seen when in place or during placement, making them easier to handle during surgical procedures than colorless ones.

In general, the compositions of the invention have improved biocompatible and physical properties over previous compounds. Therefore the compositions of the invention are especially useful in methods of preventing adhesion formation between injured tissues. One or more of the compositions of the invention can be placed between or among injured tissues that tend to form adhesions (e.g., surgical incisions and trauma) in an amount sufficient to prevent adhesions of the tissues during the healing process. The compositions act as a temporary barrier between the tissues and remain in place long enough so that once the composition has been reabsorbed and the tissues come into contact, the tissues no longer have the tendency to adhere.

Additional uses include designing nerve guides by forming the foams, films or gels into tubes or matrices for guidance of axons following nerve trauma, to foster growth cone elongation while reducing the risk of neuroma formation. They are also useful as scaffolding for cell proliferation and migration, e.g., skin regeneration, as well as tendon, ligament and cartilage regeneration. These substances are also suitable as a vehicle for drug delivery, since the drug may be introduced either before or after the biocompatible composition has been formed, allowing a controlled release of the drug to be administered.

The water-insoluble polyanionic polysaccharide compositions combined with the hydrophobic bioabsorbable polymers have the following additional advantages over uncoated, chemically modified or unmodified polyanionic polysaccharides compositions: improved mechanical properties in both the dry and wet states, making the products stronger and easier to handle and resulting in a longer in vivo residence time; slower hydration of the polyanionic polysaccharide component to maintain the adhesive properties and placement of the compositions; and improved efficacy in preventing post-surgical adhesions due to the addition of the hydrophobic bioabsorbable polymer component. The compositions can be processed with a hydrophilic side that adheres to tissue and one non-adhesive, hydrophobic side. The hydrophobic side will slow hydration of the hydrophilic side, which will adhere to tissue while the hydrophobic side will prevent other tissue, surgical instruments, and gloves from adhering to the composition.

Other features and advantages will be apparent from the following detailed description and from the claims.

DETAILED DESCRIPTION

Polyanionic polysaceharides and their salts may be obtained from a variety of standard commercial sources. Water-insoluble polyanionic polysaccharide gels, films, and foams can be prepared by any method for use in this invention. The gels may be generated via the formation of covalent intra- and inter-chain crosslinks as previously described (e.g., see Sparer et al., supra; DeBelder et al., supra; Balazs et al. supra; Malson et al., supra; and Prestwich et al. EP Publication No. 0416250A2, 1991). Alternatively, water-insoluble gels which do not contain covalent cross-links between the polyanionic polysaccharide molecules may be formed using the methods described in Hamilton et al., U.S. Pat. No. 4,937,270; Burns et al., U.S. Pat. No. 5,017,229, U.S. Pat. No. 6,030,958, and U.S. Pat. No. 5,760,200 (all of the above hereby incorporated by reference).

Activated Polyanionic Polysaccharides

A polyanionic polysaccharide is said to be "activated", as that term is used herein, when it is treated in an aqueous mixture in a manner that renders the carboxyl groups on the polyanionic polysaccharide vulnerable to nucleophilic attack; and an "activating agent" is a substance that, in an aqueous mixture including a polyanionic polysaccharide, causes the polyanionic polysaccharide to become so activated.

Polyanionic polysaccharide gels, films, and foams are prepared generally by mixing at least one polyanionic polysaccharide (e.g., HA, CMC, CMA) with an activating agent to form a water-insoluble material. Preferred activating agents include the carbodiimides, 1-(-3-dimethylaminopropyl)-3-ethylcarbodiimide (EDC) and 1-(-3-dimethylaminopropyl)-3-ethylcarbodiimide methiodide (ETC). The reaction may be carried out at a pH between 3.5 and 8, with optimal reaction conditions occurring between pH 4.7 and 5.1. The polysaccharide molecular weight used in the reaction may range from $9.0 \times 10^4$ to $3.0 \times 10^6$ daltons, but preferably is between $2.5 \times 10^5$ to $1.0 \times 10^6$ daltons. The preferred molar ratio of polysaccharide to activating agent is at least 1:1, and more preferably about 1:4. The insoluble material formed by this method may be in the form of a gel or in the form of fibers and can be used directly for adhesion prevention or drug delivery, or can be cast onto flat molds and either air-dried or lyophilized to yield thin films or foams.

Bop reagent-activated Polyanionic Polysaccharides

Polyanionic polysaccharide water-insoluble gels, films, and foams are also prepared generally by dissolving at least one polyanionic polysaccharide (e.g. HA, CMC, CMA) in an aqueous mixture; activating the polyanionic polysaccharide with an activating agent such as benzotriazole-1-yloxytris(dimethylamino)phosphonium hexafluorophosphate (Bop-reagent); and reacting the activated polyanionic polysaccharide with a suitable nucleophile to form the desired insoluble composition.

Preferred nucleophiles which are capable of reacting with the activated polyanionic polysaccharide include amino acid amides (preferably leucinamide hydrochloride), monofunctional amines (preferably 3-amino-1-propanol), amino acid esters (preferably a methyl ester or a butyl ester, including t-butyl ester), amino alcohols, amino thiols, amino phenols, amino cathechols, amino acids, salts of amino acids, peptides, proteins and other ambident nucleophilic compounds in which only one electron rich moiety reacts as a nucleophile with the activated polyanionic polysaccharide.

The reaction may be carried out at a pH between 3.5 and 8, with optimal reaction conditions between pH 4.6 and 5.0. The molecular weight of the polyanionic polysaccharide used in the reaction may range from $6.0 \times 10^2$ to $4 \times 10^6$ daltons, but preferably greater than $5 \times 10^5$ daltons. The preferred reagent stoichiometry is at least 0.1 molar equivalents of activating agent per molar equivalent of polyanionic polysaccharide, and at least 1 molar equivalent of nucleophile per molar equivalent of polyanionic polysaccharide.

One major unexpected advantage of the BOP activation of polyanionic polysaccharide is that the molecular weight of the polyanionic polysaccharide is not decreased upon coupling to the nucleophile. This result is in contrast to reactions involving carbodiimides solely, in which we observe a decrease in HA molecular weight upon nucleophilic coupling.

Modified Carbodiimide-Activated Polyanionic Polysaccharides

Polyanionic polysaccharide water-insoluble gels, films, and foams are prepared generally by dissolving at least one polyanionic polysaccharide (e.g., HA, CMC, CMA), in an aqueous mixture; activating the polyanionic polysaccharide with an activating agent such as a diimide, e.g. EDC or ETC; modifying the activated polyanionic polysaccharide with a modifying compound such as 1-hydroxybenzotriazole hydrate (HOBt), 1-hydroxybenzotriazole monohydrate or one of the other compounds described above; and reacting the activated polyanionic polysaccharide with a suitable nucleophile to form the desired insoluble composition. In the case where the activating agent used is a diimide, the modifying compound reacts with the intermediate O-acylisourea to form a new active carbonyl group capable of being transferred to a nucleophile.

The molecular weight range of the polyanionic polysaccharide used in the reaction may be $6.0 \times 10^2$ to $4.0 \times 10^6$ daltons, but preferably is greater than $5.0 \times 10^5$ daltons. The preferred reagent stoichiometry is at least 0.1 molar equivalents of a activating compound per molar equivalent of polyanionic polysaccharide, and more preferably at least 1:1. The preferred reagent stoichiometry also encompasses at least one molar equivalent of modifying compound per molar equivalent of activating agent. The reaction with the activating agent may be carried out at a pH between 3.5 and 8, with optimal reaction conditions occurring between 4.0 and 4.8. The modification of the polyanionic polysaccharide with the modifying compound is carried out at a pH between 3.0 and 8.0, with optimal modification conditions occurring between pH 3.3 and 4.5.

Foams and films of compositions containing soluble polyanionic polysaccharides and their derivatives can be generated by lyophilizing or freeze drying the solution.

Compositions containing water-insoluble polyanionic polysaccharide composition can also be treated to generate the desired film, foam, powder, or fibers. For example, to obtain films, the reaction mixture is typically poured into a vessel, e.g., a tray, having the desired size and shape and allowed to air dry.

Alternatively a film can be formed by compressing a water-insoluble gel under conditions that permit escape of water, as, for example, by compressing the water-insoluble gel between two surfaces, at least one of which is porous, as described, for example, in EPO 0 193 510.

Another alternative method of producing sheets of the material is to subject it to freeze drying. The pore size of the final product can be controlled by adjusting the initial freezing temperature and drying conditions. Curved surfaces and other shapes can be produced in a similar manner by initially casting the water-insoluble gel onto a negative image surface and then processing as described. The dried sheet can be processed further, if desired, by pressing to a defined thickness, e.g., in a Carver laboratory press. This is particularly useful for applications requiring placement of a thin film between anatomical structures where space is limited, and for imparting additional mechanical strength.

The formation of foams, fibers and other shapes or articles can also be accomplished using techniques well-known in the plastics and textile industries.

For instance, foams of the water-insoluble polysaccharide derivatives can be generated by freeze drying procedures that are well known in the art, e.g., Yannas et al., (U.S. Pat. No. 4,280,954) and Dagalakis et al., (1980, *J. Biomed. Mater. Res.*, vol. 14, p. 511–528), describe methods of freeze drying collagen-mucopolysaccharide composites and controlling pore structure. Typical conditions are temperatures below −20° C. and a vacuum below 250 mTorr.

Fibers of the water-insoluble polysaccharide derivatives can be made by wet spinning procedures that are well known in the art. For example, Rupprecht (1979, *Acta Chem. Scand.*, vol. 33, p. 779–780) describes the wet spinning of aqueous hyaluronic acid solutions into an ethanol coagulation bath to form fibers. Alternatively, fibers of the hydrophobic bioabsorbable polymers can be made by more conventional melt spinning techniques that are well known in the art. For example, Wasserman et al. (U.S. Pat. Nos. 3,792,010 and 3,839,297) describe the manufacture of monofilament and braided polyester sutures of lactide-glycolidei copolymers. The fibers can be made into fabrics by knitting and weaving techniques well known in the art.

The film and foam derivatives of polyanionic polysaccharide compositions can be strengthened by dehydrothermal treatment (DHT: 95–105° C. at 200–760 mm Hg for 6–24 hrs) and combined with hydrophobic bioabsorbable polymers. For example, bioabsorbable polymers such as polyglycolide (PGA), polylactide (PLA), and copolymers of PGA/PLA are dissolved in volatile solvents such as methylene chloride, acetone, ethylacetate, tetrahydrofuran, n-methyl-pyrrolidone at concentrations of 0.5–50.0% w/w with a preferred range of 1%–3% (w/w). Various ratios of PGA and PLA can be used including 100% PGA, 85% PGA:15% PLA, 50% PGA:50% PLA, and 100% PLA; 1:1 PGA:PLA is preferred. Additionally, other hydrophobic bioabsorbable polymers such as polydioxanones, polyorthoesters, polyestercarbonates, polylactones (especially polycaprolactone) and polyhydroxybutyrate/valerate can be used alone or as copolymers, especially copolymers of PLA and polycaprolactone. These solutions are then sprayed onto the polyanionic polysaccharide based device using spraying devices such as a small chromatography sprayer with compressed air or argon gas at 2–20 psi to achieve a 5–100% weight gain. Coated foams can be pressed into thin membranes at 1.0–5.0 metric tons employing a Carver laboratory press with 1–50 mm spacers or left unpressed as thick foams.

In one alternative method, the polysaccharide-based materials and hydrophobic bioabsorbable polymers are laminated together by heat-pressing a form of the polymer (film, foam, mesh, etc.) onto a polyanionic polysaccharide foam or film. The preferred conditions of lamination depend on the thermal properties of the various hydrophobic polymers but generally fall within the following ranges: 40–230° C. at 0–8 metric tons of compression for 0–5 minutes. In addition, the hydrophobic polymer can be rendered more hydrophilic following lamination by plasma treatment.

In a second alternative method, bioabsorbable polymer fibers are incorporated into the polysaccharide-based materials by cutting or chopping the fibers to specific sizes and dispersing them into polysaccharide-based solutions before casting or lyophilizing into films or foams. The bioabsorbable-polymer fibers can also be laid onto a substrate as a mesh or matte and then polysaccharide-based solutions can be cast on top.

In a third method, the polysaccharide-based films and foams are coated with hydrophobic polymers by means other than the spray-coating method described above. For example, bioabsorbable polymers such as PGA, PLA, and copolymers of PGA/PLA, PLA/polycaprolactone, and PGA/polycaprolactone can be dissolved in organic solvents at concentrations of 0.5–50%, preferably 1.0–3.0%. The polymer solution can then be spread with a drawdown knife or cast on the surface of a polysaccharide-based film or foam and then dried. Alternatively, the water-insoluble polysaccharide-based devices can be dipped or soaked in the polymer solution and then allowed to air dry to achieve incorporation.

In still another method, composite fibers can be made which contain a water-insoluble polysaccharide derivative core and a hydrophobic bioabsorbable polymer coating. Aqueous solutions containing polysaccharide derivatives are extruded through a spinneret or syringe needle into a coagulation bath containing a bioabsorbable polymer solution, such as PGA/PLA, PLA/polycaprolactone, or PGA/polycaprolactone dissolved in organic solvent. The water-insoluble polysaccharide-based material precipitates in the coagulation bath and is simultaneously coated with bioabsorbable polymer. Alternatively, the water-insoluble polysaccharide-based fiber can be coated with bioabsorbable hydrophobic polymer after the coagulation stage of the wet-spinning process by drawing the polysaccharide derivative fiber through a solution of bioabsorbable hydrophobic polymer.

The invention is described in more detail in the following examples. These examples are given by way of illustration and are not intended to limit the invention except as set forth in the claims.

EXAMPLE 1

A solution of HA (5.5 g, 13.7 moles, MW 2,350,000) and CMC (2.5 g, 9.7 moles, MW 250,000) in water (1 L) was pH adjusted to 4.74 with 0.1 M HCl, after which 1-(-3-dimethylaminopropyl)-3-ethylcarbodiimide (10.6 g, 55.5 moles) was added. The pH was maintained between 4.6–5.1 for 1 hour by the addition of 0.1 M HCl. The reacted solution was dialyzed in membrane tubing (MW cut off 12–14,000) for 24 hours against deionized water, pH 4.0. The purified chemically modified HA/CMC solution was poured into stainless steel trays and lyophilized into solid foam sheets. Specifically, the temperature of the product was lowered at a rate of 0.1° C./min to −20° C. Then the drying cycle was executed with vacuum set at 150 mTorr and shelf temperature raised at 0.1° C./min to 0° C. The temperature was held at 0° C. for 900 minutes and then raised at 0.1° C./min to 27° C. The foams were then strengthened by dehydrothermal treatment (105° C. at 200 μm Hg for 24 hours). The foams were then weighed and placed in a polypropylene frame prior to coating.

Lactide/Glycolide copolymer (2.0 g, 50% PGA: 50% PLA Medisorb Corporation) was dissolved in methylene chloride (100 ml). This coating solution was then sprayed at 5 psi onto the foams using a small chromatography sprayer equipped with compressed air. A weight gain of 10–15% was achieved by varying the duration of spraying time based on the size of the foam and the calculated flow rate of spray. Evaporation of the methylene chloride solvent was slowed by covering the foam immediately after spraying. After drying, the foams were pressed (1 metric ton, 15 sec, 0.25 mm spacer) into thin films, cut, packged, and gamma-irradiated at 2.5 Mrad.

Material prepared by this method was then evaluated for prevention of post-surgical adhesions in a rat cecal abrasion model (Goldberg et al., In *Gynecologic Surgery and Adhesion Prevention*. Willey-Liss, pp. 191–204, 1993). HA/CMC membranes or foams, Interceed TC7 membranes (Johnson & Johnson), and HA/CMC films or foams which were coated with PGA:PLA polymer, were placed around surgically abraded rat ceca, and compared to non-treated controls (animals whose ceca were abraded but did not receive any treatment). The results from two studies are shown in Table 1.

TABLE 1

EVALUATION OF HA-BASED DEVICES AND INTERCEED TC7 FOR POSTOPERATIVE ADHESION FORMATION

| Test Group | % of Animals with Adhesions ≧ Grade 2 | Average Incidence of Adhesions |
| --- | --- | --- |
| 1. Control (No Treatment) | 100% (5/5) | 2.8 |
| HA/CMC Foam w/PGA: PLA Coating Interceed TC7 | 0% (0/5) | 0.0 |
| | 60% (3/5) | 0.8 |
| 2. Control (No Treatment) | 100% (4/4) | 1.4 |
| HA/CMC Film | 60% (3/5) | 0.8 |
| HA/CMC Foam | 20% (1/5) | 1.0 |
| HA/CMC Foam w/PGA: PLA Coating | 0% (0/5) | 0.2 |
| Interceed TC7 | 40% (2/5) | 1.4 |

These results demonstrate that films and foams coated with the PGA:PLA polymer consistently reduced adhesion formation compared to the control group, to animals that received Interceed TC7, and to animals that received either HA/CMC films or foams.

EXAMPLE 2

In this example, modified HA/CMC powder made according to the methods of U.S. Pat. No. 4,937,270 (4.5 g) was suspended in distilled water (450 ml) using a high speed blender (20 minutes at 1000 rpm). The resuspended solution was poured into Teflon coated stainless steel trays and lyophilized into solid foam sheets. Lyophilization was performed as described in Example 1.

A thin film of polylactide copolymer (90% PLA-L:10% PLA-DL) was obtained from Medisorb Corporation. The HA/CMC foam and polylactide film were then heat-pressed together into thin sheets (155–165° C., 15–30 seconds, 1 metric ton, 0.30 mm spacer). The wet tensile properties of the compositions were evaluated with an Instron™ Universal Testing System Model 4201 equipped with a 500 g load cell. A test chamber was specifically designed for measuring the mechanical properties of the samples while immersed in a physiological environment. Results, shown in Table 2, demonstrate that the load at break under wet conditions was significantly improved for the HA/CMC foams that were laminated with PLA. In this experiment, the samples were tested in a specially designed environmental chamber containing in a physiological environment (buffered saline at pH 7 at 25° C.). The initial grip separation was 25 mm and the crosshead speed was 5 mm/min.

TABLE 2

WET MECHANICAL PROPERTIES OF HA/CMC:PGA/PLA COMPOSITIONS

| Sample | n | Wet Load (N) | Wet Elong. (%) |
| --- | --- | --- | --- |
| F30719 HA/CMC Foam (Control) | 6 | 0.2 ± 0.06 | 38.6 ± 3.4 |
| F30719-3 HA/CMC Foam w/PGA Mesh | 2 | 28.2 ± 20.6 | 112.2 ± 34.9 |
| F30719-4 HA/CMC Foam:PLA Film Laminate | 3 | 12.7 ± 3.7 | 4.1 ± 1/5 |

EXAMPLE 3

In this example, modified HA/CMC powder (4.5 g) was suspended in distilled water (450 ml) using a high speed blender (20 min at 1000 rpm). A piece of 100% PGA mesh was placed in a Teflon coated stainless steel tray. The resuspended HA/CMC solution was poured into the tray and lyophilized into a solid foam sheet according to the procedure described in Example 1. The foam and mesh composition was pressed (1 metric ton, 15 seconds, 0.25 mm spacer) into thin sheets and strengthened by dehydrothermal treatment (100° C. for 6 hrs). The wet tensile properties of the composition were evaluated and are shown in Table 2. The wet strength of the composition was much greater than the strength of the initial HA/CMC foam.

The results from Examples 2 and 3 indicate that the composite of the HA/CMC foam and the hydrophobic bioabsorbable polymers have much greater strength under hydrated conditions (wet load) than HA/CMC foam without the hydrophobic bioabsorbable polymer.

EXAMPLE 4

Hyaluronic acid (5.5 g, 13.7 moles, MW 2,350,000) and carboxymethylcellulose (2.5 g, 9.7 moles, MW 250,000) were dissolved in one liter of water, and the pH of the solution was adjusted to 4.75 with 0.1 M HC1. 1-(-3-dimethylaminopropyl)-3-ethylcarbodiimide (10.6 g, 55.5 moles) was then added, and the solution was maintained at a pH between 4.6–5.1 for 1 hour by the addition of 0.1 M HC1. The reacted solution was then dialyzed (MW cut off 12–14,000) against deionized water, pH 4.0. The purified reaction mixture was then poured into a polystyrene tray at a casting density of 2.2 g HA/CMC/ft$^2$.

Polyglycolic acid fibers were prepared by cutting Dexon sutures. The fibers were sonicated in water to produce a mat-like material with a high degree of fiber entanglement. This material was then hydrated in methylene chloride to allow the fibers to coalesce after which the fibers were air dried. The resulting mat-like material was placed on top of the cast HA/CMC reaction mixture at a density of 0.1 g/ft$^2$. The entire composition was then air dried to form a bilayer of PGA fibers and modified HA/CMC.

EXAMPLE 5

Procedures are well known in the art for seeding and growing mammalian cells on physical matrices. The purpose of the matrix is to give support to the cells, to allow the cells to migrate through the matrix, to allow easy handling of the cells for implantation, and to help keep the cells in place once implanted. The novel PAS composites of the present invention can be used as a matrix for this purpose. In one example, the PAS derivative hydrophobic bioabsorbable matrix formed as described in Example 2 is cut to size and shape of a cell culture dish. Mammalian fibroblasts, isolated from skin by trypsinization, or obtained from a standard cell lines (e.g., available from the ATCC), are cultured at 37° C. in a 5% $CO_2$ atmosphere and approximately 95% to 100% relative humidity. Once they are grown, these fibroblasts are removed from the culture flask by trypsinization and washed with culture medium containing fetal calf serum. The cell density is adjusted to approximately $10^4$ to $10^6$ cells/ml.

The matrix is placed in the culture dish with the hydrophobic side down; the cell suspension is placed on the matrix in the cell culture dish, ensuring complete coverage of the matrix; and the admixture is incubated at 37° C. and 5% $CO_2$. The cells are grown on the matrix until cell proliferation throughout the matrix has occurred. The matrix infiltrated with fibroblasts can then be placed on dermal ulcers, burns, and wounds to aid in wound healing or to act as a skin substitute. The preferred source of the fibroblasts is autologous tissue. However, in cases where the use of autologous tissue is not convenient, or the tissue is not readily available, allogeneic or even xenogeneic fibroblasts can be used. Biocompatible matrices containing xenogeneic or allogeneic cells are useful for providing extracellular scaffolding to aid in the migration and establishment of autologous cells during the healing process. Biocompatible matrices which contain non-autologous cells can also be co-administered (e.g., at the same time, or immediately following placement of the matrix) with standard immunosuppressive therapies (e.g., steroids, azathioprine, cyclosporine) if desired.

Further, the biocompatible matrices can also be impregnated with drugs or growth factors to prevent infection at the placement site, and to enhance the growth of the cells, respectively. For example, fibroblast infiltrated matrices containing $TGF\beta_2$ are expected to be especially useful in promoting growth of epidermal tissues.

We have shown that these devices have improved handling properties and reduce the incidence of post-surgical adhesions in experimental animal models more successfully than existing products. In these experiments, HA/CMC:PGA/PLA compositions reduced adhesion formation when compared to animals that received HA/CMC devices, Interceed TC7 film (marketed by Johnson & Johnson for adhesion prevention), or untreated control animals.

The water-insoluble compositions of the invention can be used in abdominal operations, operations of the urogenital tracts, nerve surgery, joint operations and ophthalmological operations for purposes requiring maintenance of placement of tissues without adhesion formation. They can also be of use as sealing agents in anastomotic sites for catheters, bowel anastomoses, endoscopic surgical procedures, vascular grafts, and any prosthetic device requiring gluing together or sealing of potential leakage sites; as a new biocompatible fiber for processing into thread, braids, woven and non-woven webs, weaves and mats, and sutures for wound closure; sclerosing agents for varicose vein removal, tumors, and aneurisms; artificial extracellular matrix materials for cell and tissue replacement for skin, tendon, ligament, bone, cartilage, and other tissues and organs.

The time period required to effectively prevent adhesion will vary according to the type of surgery or injury involved. Generally, the tissues should remain separated for at least 48 hours, and preferably, for a period of at least 7 days. Accordingly, the rate of diffusion of the composition used in any particular situation can be varied, for example, by altering the extent of the composition's solubility or insolubility, by varying the density of the polyanionic polysaccharide used, or by varying the thickness of the film, foam, gel, or fiber used. These characteristics can be altered by routine procedures, and the properties desired for any type of surgery or trauma can be determined by routine experimentation using the guidance of the examples described herein.

Films, foams, or gels of the invention can further be used for drug delivery. For example, in the case where rapid, localized delivery is desirable, water-soluble compositions within the invention can be used. Alternatively, compositions containing water-insoluble polyanionic polysaccharides are useful for sustained release drug delivery. The drug to be delivered can be dispersed within the composition, or can be covalently bonded to the foam, film, or gel as described, for example, in R.V. Sparer et al., 1983, Chapter 6, pages 107–119, in T.J. Roseman et al., *Controlled Release Delivery Systems*, Marcel Dekker, Inc., New York; and the foam, film, or gel can then be implanted or injected at the locus where delivery is desired.

Although the foregoing invention has been described in some detail by way of illustration and example, it is understood that other modifications, embodiments, and equivalents will be apparent to those of ordinary skill in the art without departing from the scope of the appended claims.

We claim:

1. A water-insoluble biocompatible composition comprising a water-insoluble derivative of a first polyanionic polysaccharide and fibers of a hydrophobic bioabsorbable polymer, wherein the derivative is formed by reacting the polyanionic polysaccharide at least with an activating agent to form a derivative bearing i) an amide or amine group or ii) N-acyl urea group.

2. The composition of claim 1 wherein said derivative is formed by reacting the polyanionic polysaccharide with an activating agent and a nucleophile.

3. The composition of claim 1, wherein said polyanionic polysaccharide is chosen from the group consisting of carboxymethylcellulose, carboxymethylamylose, hyaluronic acid, chondroitin-6-sulfate, heparin, heparin sulfate, and dermatan sulfate.

4. The composition of claim 3, wherein said polyanionic polysaccharide is carboxymethylamylose.

5. The composition of claim 3, wherein said polyanionic polysaccharide is carboxymethylcellulose.

6. The composition of claim 3 wherein said polyanionic polysaccharide is hyaluronic acid.

7. The composition of claim 1 wherein said biocompatible composition comprises two or more a water-insoluble derivative of a second polyanionic polysaccharides.

8. The composition of claim 7 wherein first and second polyanionic polysaccharides are hyaluronic acid and carboxymethylcellulose.

9. The composition of claim 1, wherein said hydrophobic bioabsorbable polymer is chosen from the group consisting of polyglycolide, polylactide, polydioxanones, polyestercarbonates, polyhydroxyalkonates, polylactones, and copolymers thereof.

10. The composition of claim 9 wherein said hydrophobic bioabsorbable polymer is polyglycolide.

11. The composition of claim 9 wherein said hydrophobic bioabsorbable polymer is polylactide.

12. The composition of claim 9 wherein said hydrophobic bioabsorbable polymer is a copolymer of polyglycolide and polylactide.

13. The composition of claim 9 wherein said hydrophobic bioabsorbable polymer is a copolymer of polyglycolide/polycaprolactone.

14. The composition of claim 9 wherein said hydrophobic bioabsorbable polymer is a copolymer of polylactide/polycaprolactone.

15. The composition of claim 1, wherein said composition is in the form of a membrane.

16. The composition of claim 1, wherein said composition is in the form of a foam.

17. The composition of claim 1 wherein said form a mesh or matte.

18. The composition of claim 1, further comprising a drug.

19. The composition of claim 18 wherein said drug is chosen from the group consisting of proteins, biopolymers, steroids, non-steroidal anti-inflammatory drugs, cytotoxic agents, antibiotics, and oligonucleotides.

20. The composition of claim 7, further comprising a drug.

21. The composition of claim 20, wherein said drug is chosen from the group consisting of proteins, biopolymers, steroids, non-steroidal anti-inflammatory drugs, cytotoxic agents, antibiotics, and oligonucleotides.

22. The composition of claim 1 further comprising biological cells.

23. The composition of claim 22, wherein said composition is admixed with said cells.

24. The composition of claim 22, wherein said composition is infiltrated with said cells.

25. The composition of claim 22, wherein said cells are derived from a mammal.

26. The composition of claim 25, wherein said mammal is a human.

27. The composition of claim 22, wherein said cells comprise fibroblasts.

28. The composition of claim 22, wherein said cells comprise osteocytes.

29. The composition of claim 22, wherein said cells comprise chondrocytes.

30. The composition of claim 22, wherein said cells comprise keratinocytes.

31. The composition of claim 22, wherein said cells comprise tenocytes.

32. The composition of claim 22, wherein said cells comprise non-differentiated mesenchymal cells.

33. The composition of claim 22, wherein said cells comprise a mixture of at least two cell types.

34. The composition of claim 22, further comprising a drug.

35. The composition of claim 34, wherein said drug is a growth factor.

36. The composition of claim 34 wherein said drug is an antibiotic.

37. The composition of claim 7, further comprising biological cells.

38. The composition of claim 37, wherein said composition is admixed with said cells.

39. The composition of claim 37, wherein said composition is infiltrated with said cells.

40. The composition of claim 37, wherein said cells are derived from a mammal.

41. The composition of claim 40, wherein said mammal is a human.

42. The composition of claim 37, wherein said cells comprise fibroblasts.

43. The composition of claim 37, wherein said cells comprise osteocytes.

44. The composition of claim 37, wherein said cells comprise chondrocytes.

45. The composition of claim 37, wherein said cells comprise keratinocytes.

46. The composition of claim 37, wherein said cells comprise tenocytes.

47. The composition of claim 37, wherein said cells comprise non-differentiated mesenchymal cells.

48. The composition of claim 37, wherein said cells comprise a mixture of at least two cell types.

49. The composition of claim 37, further comprising a drug.

50. The composition of claim 49, wherein said drug is a growth factor.

51. The composition of claim 49, wherein said drug is an antibiotic.

52. The composition of claim 1 wherein said activating agent is a carbodiimide.

53. The composition of claim 52 wherein said carbodiimide is 1-(-3-dimethylaminopropyl)-3-ethylcarbodiimide (EDC).

54. The composition of claim 52 wherein said carbodiimide is 1-(-3-dimethylaminopropyl)-3-ethylcarbodiimide methiodide (ETC).

55. The composition of claim 7 wherein said second water-insoluble polyanionic polysaccharide is formed by reacting the second polyanionic polysaccharide with an activating agent.

56. The composition of claim 55 wherein said activating agent is a carbodiimide.

57. The composition of claim 56 wherein said carbodiimide is 1-(-3-dimethylaminopropyl)-3-ethylcarbodiimide (EDC).

58. The composition of claim 56 wherein said carbodiimide is 1-(-3-dimethylaminopropyl)-3-ethylcarbodiimide methiodide (ETC).

59. An article comprising the composition of claim 1 wherein the fibers form a mesh or matte.

60. The article of claim 59 having the shape of a sheet.

61. The article of claim 59 having the shape of a tube.

* * * * *